(12) United States Patent
Adams et al.

(10) Patent No.: US 7,790,104 B2
(45) Date of Patent: Sep. 7, 2010

(54) METHODS AND APPARATUS FOR DECONTAMINATING ENCLOSED SPACES

(75) Inventors: Nicholas Mark Turner Adams, Clanville (GB); David Watling, Dorking (GB)

(73) Assignee: Bioquell UK Limited (GB)

( * ) Notice: Subject to any disclaimer, the term of this patent is extended or adjusted under 35 U.S.C. 154(b) by 487 days.

(21) Appl. No.: 10/509,192

(22) PCT Filed: Mar. 28, 2003

(86) PCT No.: PCT/GB03/01386

§ 371 (c)(1),
(2), (4) Date: Sep. 24, 2004

(87) PCT Pub. No.: WO03/082355

PCT Pub. Date: Oct. 9, 2003

(65) Prior Publication Data

US 2005/0175500 A1    Aug. 11, 2005

(30) Foreign Application Priority Data

Mar. 28, 2002   (GB)   .................... 0207452.4
May 22, 2002   (GB)   .................... 0211851.1

(51) Int. Cl.
*A61L 9/00*   (2006.01)
*A61L 2/24*   (2006.01)
*A61L 2/00*   (2006.01)

(52) U.S. Cl. .............................. 422/29; 422/3; 422/292

(58) Field of Classification Search ................... 422/29, 422/3

See application file for complete search history.

(56) References Cited

U.S. PATENT DOCUMENTS 4,244,712 A * 1/1981 Tongret ..................... 96/25

(Continued)

FOREIGN PATENT DOCUMENTS

CH    689 178 A5    11/1998

(Continued)

OTHER PUBLICATIONS

David Watling et al., *Theoretical Analysis of the Condensation of Hydrogen Peroxide Gas and Water Vapour as Used in Surface Decontamination,* PDA Journal of Pharmaceutical Science and Technology, vol. 56, No. 6, Nov./Dec. 2002, pp. 291-299.

(Continued)

*Primary Examiner*—Sean E Conley
*Assistant Examiner*—Kevin C Joyner
(74) *Attorney, Agent, or Firm*—Workman Nydegger

(57) ABSTRACT

The disclosure relates to a portable apparatus for decontaminating an enclosed room or other space which includes a passageway having an air inlet at one end and an outlet at the other end. A pump causes a flow of air through the passageway from the inlet to the outlet. A heater heats the air flowing through the passageway to a predetermined temperature, a flash evaporator being in communication with the passageway. Liquid decontaminant is pumped from a supply of decontaminant to the evaporator to be evaporated and for the evaporant to be delivered to the air flow in the passage to flow in the air flow from the outlet to the rooms to be decontaminated. A universally rotating nozzle is provided at the outlet to distribute the decontaminant containing air throughout the enclosure.

40 Claims, 10 Drawing Sheets

U.S. PATENT DOCUMENTS

Figure 1:
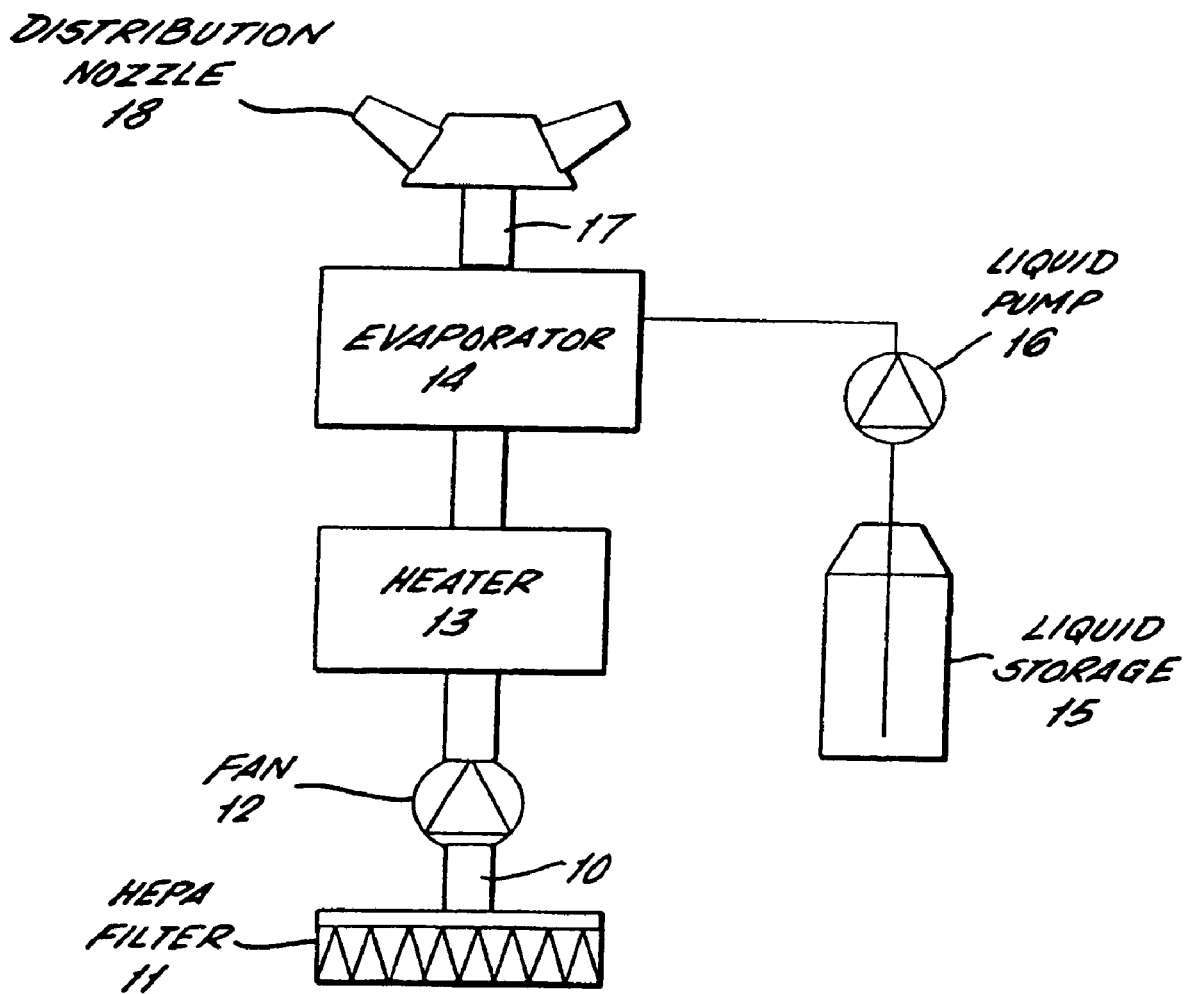
Figure 2:
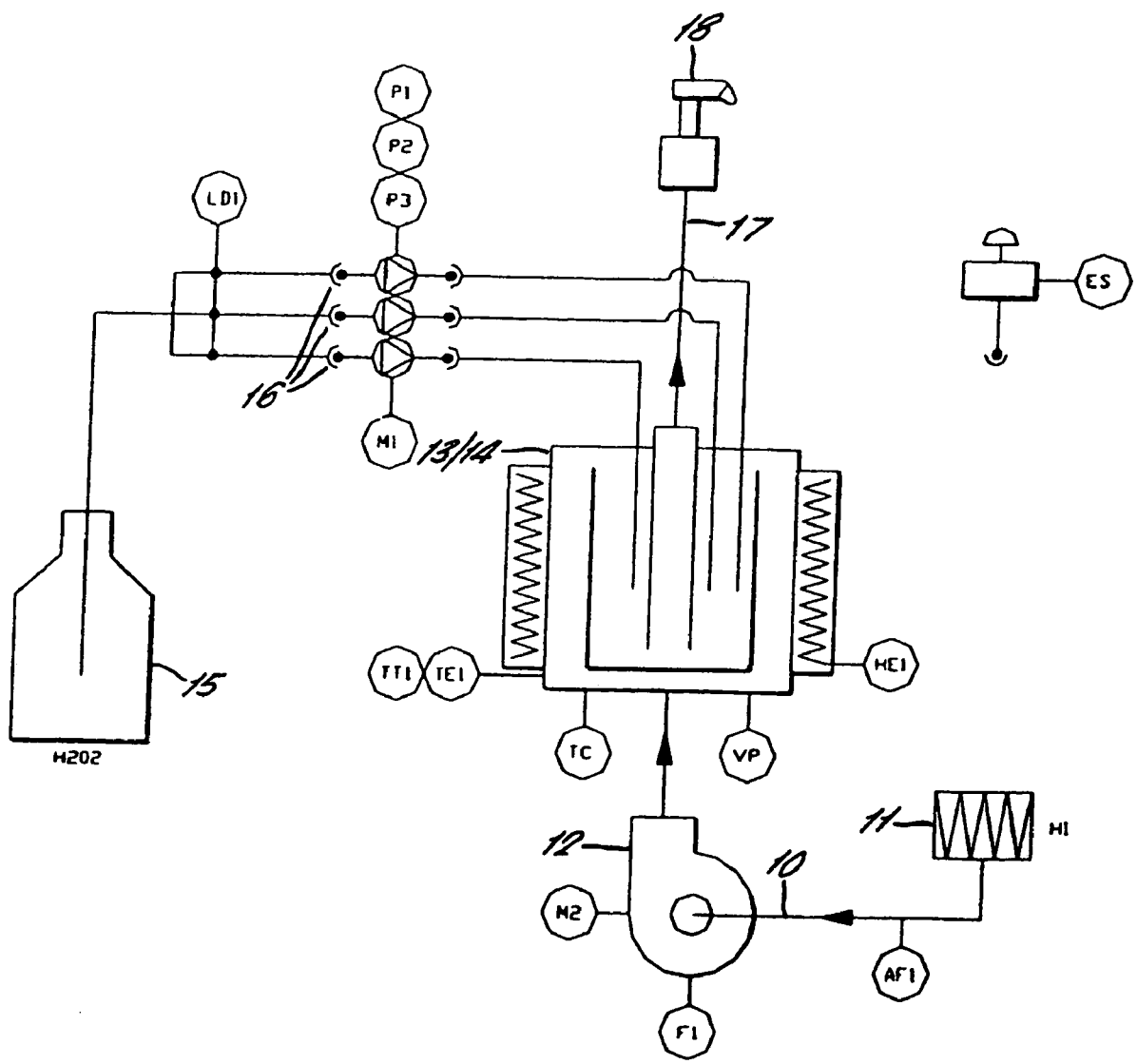

| | | | |
|---|---|---|---|
| 4,863,688 A | | 9/1989 | Schmidt et al. |
| 5,173,258 A | * | 12/1992 | Childers ................... 422/27 |
| 5,480,615 A | * | 1/1996 | Curry ..................... 422/124 |
| 6,096,265 A | | 8/2000 | Mezger et al. |
| 6,589,479 B2 | * | 7/2003 | Dufresne et al. ........... 422/28 |
| 6,630,105 B1 | * | 10/2003 | O'Neill et al. ............. 422/24 |
| 6,840,744 B2 | | 1/2005 | Watling |
| 7,014,813 B1 | | 3/2006 | Watling |
| 7,025,932 B2 | | 4/2006 | Martin et al. |
| 7,186,371 B1 | | 3/2007 | Watling |

FOREIGN PATENT DOCUMENTS

| | | |
|---|---|---|
| GB | 2 354 443 A | 3/2001 |
| GB | 2 360 454 A | 9/2001 |
| JP | 54-050184 | 4/1979 |
| JP | 54-082893 | 7/1979 |
| JP | 61-234859 | 10/1986 |
| JP | 63-011163 | 1/1988 |
| JP | 03-224469 | 10/1991 |
| JP | 08-266596 | 10/1996 |
| JP | 2001-212431 | 8/2001 |
| RU | 2 054 295 C1 | 2/1996 |
| WO | WO 98/44958 | 10/1998 |
| WO | WO 00/38746 | 7/2000 |
| WO | WO 00/74734 A1 | 12/2000 |
| WO | WO 01/21223 A1 | 3/2001 |
| WO | WO 02/11774 A1 | 2/2002 |
| WO | WO 02/11864 A1 | 2/2002 |

OTHER PUBLICATIONS

Seymour S. Block, Ph.D., *Disinfection, Sterilization, and Preservation*, 5$^{th}$ Edition, Lippincott Williams & Wilkins, Dec. 200, pp. 188-189.

* cited by examiner

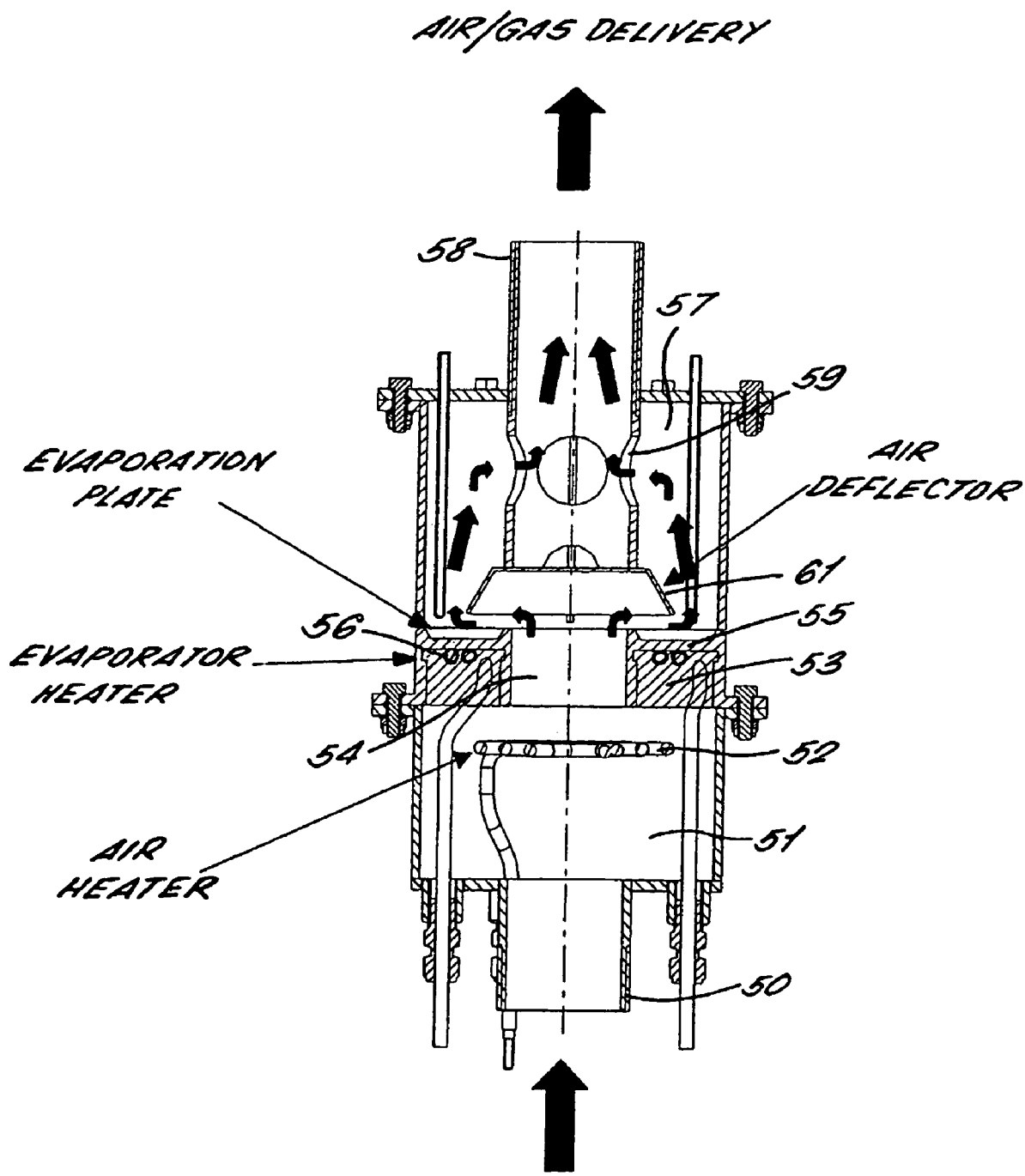

METHODS AND APPARATUS FOR DECONTAMINATING ENCLOSED SPACES

BACKGROUND OF THE INVENTION

1. Field of the Invention

This invention relates to methods and apparatus for decontaminating enclosed spaces such as hospital wards and clean rooms in which a manufacturing or other processes take place in sterile conditions.

2. Present State of the Art

Vaporised aqueous solution of hydrogen peroxide has been used to decontaminate the internal surfaces of enclosures used for aseptic processing in the pharmaceutical industry since about 1990, but it has always been difficult to use the same technology to decontaminate larger enclosed volumes such as rooms.

The conventional apparatus for decontaminating enclosures comprises a gas generator in a closed circuit including the enclosure such as described in U.S. Pat. No. 5,173,258. In this design the hydrogen peroxide and water vapours are produced by flash evaporation of an aqueous solution into a heated air stream, which then carried the gas to the space to be decontaminated. The air and mixture of gases then mixes with the air inside the chamber before being returned to the gas generator, where the gas is decomposed, dried, heated and more liquid is flash evaporated and the air mixture is returned to the chamber.

The processes performed on the returned gas are complex, and include the steps of decomposing the gas, drying and re-heating. This complete process was considered necessary because it was understood that the hydrogen peroxide gas decomposed according to a half-life rule and hence to maintain an adequate concentration inside the chamber a circulating system that decomposed the gas was thought to be necessary. Recent work by Watling, ISPE Conference Zurich, September 1999 has shown that the gas does not decompose but is stable. It is therefore not necessary to remove the returning gas from the chamber.

S.S. Block reports in the 5th Edition of Disinfection, Sterilisation and Preservation page 189 that a 3% hydrogen peroxide aqueous solution gives a log 8 reduction of *Staphylococcus aureus* in under 20 minutes. A slower rate of deactivation has been found in experimental work when exposing *Staphylococcus aureus* to gas generated from 35% solution, when the process was operated at a temperature below the dew point thus causing condensation. Under these gassing conditions the first droplets of dew form on the organism at a much higher concentration than that of the original liquid, typically about 65% w/w, the exact value depending on the moisture content of the carrier gas.

As stated above, in the conventional system the air in the chamber to be decontaminated is dried prior to injecting the decontaminating gas. This is done either to allow a high level of gas concentration to be achieved before the onset of condensation, or to operate the process avoiding condensation maintaining the gas in a dry state. The vapour pressure equations for hydrogen peroxide and water may be used to calculate the concentration of the hydrogen peroxide and water vapour that will cause condensation and hence may be used either to avoid the conditions that will cause the onset of condensation or to calculate the concentration of any condensate that may be formed as a result of passing the flash evaporated vapours into the sealed enclosure. If the RH in the chamber is high the condensation will form quickly but as a relatively weak solution. Evaporating 35% w/w hydrogen peroxide into a chamber at 20° C. and 85% RH will cause the condensate to form at in excess of 6% w/w, although the concentration of the vapour will be about 120 ppm. It is well known that 6% hydrogen peroxide is active against microorganisms and will cause bio-deactivation of surfaces. If it is intended to operate a process where condensation is formed it is therefore not necessary to reduce the humidity in the chamber under normal operating conditions as the RH will be less than 85% and hence the condensation will form at a concentration greater than 6%. The same is not true when operating a process that is intended to avoid condensation, in such a process it is essential to ensure that the moisture content of the air inside the enclosed space at the start of the process is low.

It is believed that the difference between the liquid process as reported by Block and a gaseous dew process is the rate of delivery of the hydrogen peroxide condensation. It follows that using a standard recirculating gas generator placed outside the space to be bio-decontaminated; there may not be an adequate evaporation capacity to achieve a sufficiently high condensation rate to deactivate the organism inside the chamber. The deactivation process may be enhanced by the use of mixtures of chemicals but the principal of the rate of delivery still remains. Whilst for a dry gas process the rate of delivery of hydrogen peroxide and water vapour are not so critical it is still important to evaporate the liquid as fast as is practical as this will shorten the time required to raise the gas concentration and achieve a satisfactory bio-decontamination.

An analysis of the equations governing the vapour pressure of water and hydrogen peroxide by Watling et al and published in the PDA Journal of Science and Technology November/December 2002 vol 56, No 6 291-299, shows that the gas concentration inside a chamber may be raised to the dew point by passing flash evaporated vapour into the sealed enclosure, but as soon as the dew point is reached condensation will form at a higher concentration than the evaporated liquid thus reducing the gas concentration. The gas concentration will continue to fall as more liquid is evaporated until the equilibrium vapour pressure for the evaporated liquid is reached at the temperature of the chamber.

There are two views about the mechanisms involved in the bio-decontamination using hydrogen peroxide and water vapour. The first is that it is important to ensure that the gas remains in the dry state and the second that condensation is essential. It has been well established that dry hydrogen peroxide gas at elevated temperatures will bio-deactivate microorganisms, and the same dry process has been shown to work at room temperatures. The condensation process in which the gas concentration is raised to the dew point and condensation is allowed to form appears to be faster at room temperatures.

SUMMARY OF THE INVENTION

The apparatus and method described in the present invention will work equally well with both the dry and condensation processes. When operating a dry process it is essential to monitor the water and hydrogen peroxide concentration in the gaseous phase to ensure that they remain below the saturated vapour concentrations. When operating a condensation process it is helpful to have an indication of the point during the cycle when condensation starts to form and the subsequent rate of formation. A technique and apparatus to make such a measurement of condensation is described patent application UK 0291983.1

An ideal bio-decontamination cycle is in three phases. The first phase is to bring all of the equipment to thermal stability but may also be used to adjust the relative humidity in the chamber to a pre-set level, the second is used to raise the gas concentration to the required level and maintain that concentration for a sufficient length of time to achieve the required level of bio-decontamination, and the third and last phase to reduce the concentration of the sterilant in the enclosed space to a predetermined value.

U.S. Pat. No. 4,863,688 discloses a method of selectively destroying organisms within a chamber such as an incubator comprising the steps of introducing vapour phase hydrogen peroxide into the chamber at a rate sufficient to cause a predetermined concentration of hydrogen peroxide to be reached while preventing a substantial change in pressure or condensation of the hydrogen peroxide in the chamber. When the predetermined period of time has elapsed, the vapour phase hydrogen peroxide is removed from the chamber. In a preferred embodiment disclosed an incubator is provided with a separate apparatus for producing a flow or air containing hydrogen peroxide vapour which is delivered to the incubator. Alternatively the apparatus for producing the air flow containing hydrogen peroxide vapour may be built into the incubator.

RU-C-2054295 discloses a device for sanitary treatment of air for use in livestock and poultry facilities and in various branches of industry including biological, food, light industry, chemical, coal, construction and other applications. The device includes a housing with an inlet and an outlet, a heating element, disinfected evaporator in the form of a perforated header closed at one end and enclosed in a porous sheath, the header is installed along the housing axis. The device has a reservoir containing disinfectant solution secured to the housing and connected to the open end of the evaporator. The tubular evaporator is arranged in the porous sheath along a spiral line and the heating element is mounted within the centre of the spiral.

This invention provides a method of decontaminating an enclosed space comprising the steps of providing an aqueous solution of hydrogen peroxide in the enclosed space, producing hydrogen peroxide/water vapour from said aqueous solution, creating an air stream in the enclosed space, introducing hydrogen peroxide/water vapour into the air stream, distributing the hydrogen peroxide/water vapour containing air stream throughout the space to be decontaminated and then removing the hydrogen peroxide/water vapour from the space; characterised in that the air stream is heated before hydrogen peroxide/water vapour is introduced to it, the hydrogen peroxide/water vapour is flash evaporated from an aqueous solution of hydrogen peroxide/water vapour from said supply into the air stream, and the air stream carrying the flash evaporated hydrogen peroxide/water vapour is distributed throughout the enclosed space to achieve bio-decontamination of the enclosed space.

By placing the gas generator inside the room and simply heating the carrier gas and then evaporating this sterilant into the air stream it is possible to use the available energy much more efficiently. The increase in efficiency is derived from the removal of the system for decomposing and drying the carrier gas, and also because there is no need for any pipe work to transport the carrier gas and decontaminant from an external generator.

This increased efficiency provides more energy for the primary function of heating the carrier gas and flash evaporating the liquid. The efficiency increase is so great as it allows a trebling of the rate of flash evaporation from the same energy source and hence the rate of increase in the gas concentration or the achievable rate of formation of condensation once the dew point has been reached is also trebled.

The simplified design is also much smaller and lighter than a conventional gas generator and hence considerably less expensive to manufacture. It is therefore realistic to place a number of such devices inside a sealed enclosure to be decontaminated. This reduction in size and weight makes the apparatus portable and hence makes it practical to use the same apparatus to bio-decontaminate a number of facilities either on the one site or at different locations. As stated above it is important to make measurements of the hydrogen peroxide and water vapour concentrations. To satisfy this requirement an instrument module that is placed inside the enclosed space has been devised that will also link back to the control system that is external to the enclosed space. Provision has been made within the control systems both at the gas generator(s) and the instrument module to connect a number of condensation sensors so that the process may be operated either as a dry gas or as a saturated vapour process Each simplified generator will have its own control system, which is linked to a control box external to the room and connected by a single control cable. By using a central control system, such as a laptop computer, it is possible to control a number of generators that are linked together from outside the enclosed space. With the present arrangement it is possible to control eight generators from a single laptop, should a larger number be required a second computer would be needed. It is also possible to control multiple aeration units and dehumidifiers from the same laptop computer.

Because the apparatus is portable and may therefore be used at different sites in order to ensure that the apparatus does not carry contamination from one location to another it is essential that all of the external and internal surfaces are bio-decontaminated during the gassing cycle. To achieve this objective components have been mounted in such a way to ensure that they are exposed to the sterilising gas. The tubular steel frame has been sealed and the control box is purged with the sterilising gas drawn from the room. Tests have been performed to check that following a bio-decontamination cycle all of the surfaces of the apparatus have been rendered safe.

BRIEF DESCRIPTION OF THE DRAWINGS

The following is a description of some specific embodiments of the invention, reference being made to the accompanying drawings, in which:

FIG. 1 is a wholly diagrammatic view of an apparatus for generating and delivering an air flow containing an evaporated decontaminant to an enclosed space;

FIG. 2 is a similar view to FIG. 1 showing the components of the apparatus including the evaporator, liquid sterilant supply and outlet nozzle in greater detail;

FIG. 3 is a perspective view of a portable unit embodying the apparatus of FIGS. 1 and 2;

FIG. 4 in an exploded view of the unit of FIG. 3;

FIG. 5 is a plan view of the evaporator;

FIG. 6 is a cross-sectional view on the line 6-6 of FIG. 5;

FIG. 7 is a cross-sectional view of an alternative form of evaporator;

FIG. 8 is a perspective view of a control box for the apparatus of FIGS. 3 and 4 with a lid of the box shown open;

FIG. 9 is an exploded view of a monitoring unit for use in conjunction with the apparatus of FIGS. 3 and 4; and FIGS. 10 and 11 show further embodiments.

DETAILED DESCRIPTION OF THE PREFERRED EMBODIMENTS

The gas generator apparatus will be described firstly with reference to FIGS. 1 and 2. Room air, which may or may not already contain previously supplied hydrogen peroxide and water vapour, is drawn into an inlet conduit 10 through a HEPA filter 11 by a variable speed motor driven fan 12. The HEPA filter 11 removes any particles from the air stream to ensure that the delivered air is of the correct quality when the generator is used in a clean room. The conduit delivers the air to a heater 13 where the temperature is raised to a predetermined level as described below. The heated air then passes into an evaporator 14 where a liquid sterilant comprising aqueous hydrogen peroxide is flash evaporated. By way of example, the sterilant may comprise an aqueous solution containing 30 to 35% hydrogen peroxide. If the sterilent includes peracetic acid, the proportion of hydrogen peroxide can be reduced to 15% with 0.5% peracetic acid and a balance of water. In practice the heater 13 and the evaporator 14 are combined in a single unit as shown in FIGS. 2 to 7 to which reference will be made later. The physical shape and dimensions of the combined heater/evaporator are designed to control the energy balance between that used to heat the carrier gas and that used for flash evaporation.

A supply of aqueous hydrogen peroxide liquid is stored in a container 15 and is pumped to the evaporator 14 by a liquid pump 16. The carrier gas and vapours are delivered from the evaporator through a conduit 17 to a distribution nozzle 18 for delivery of the sterilant vapour to the space to be decontaminated. The liquid container is demountable from the frame 19 to reduce the weight of the unit and make it more easily hand carried.

Figure 3:
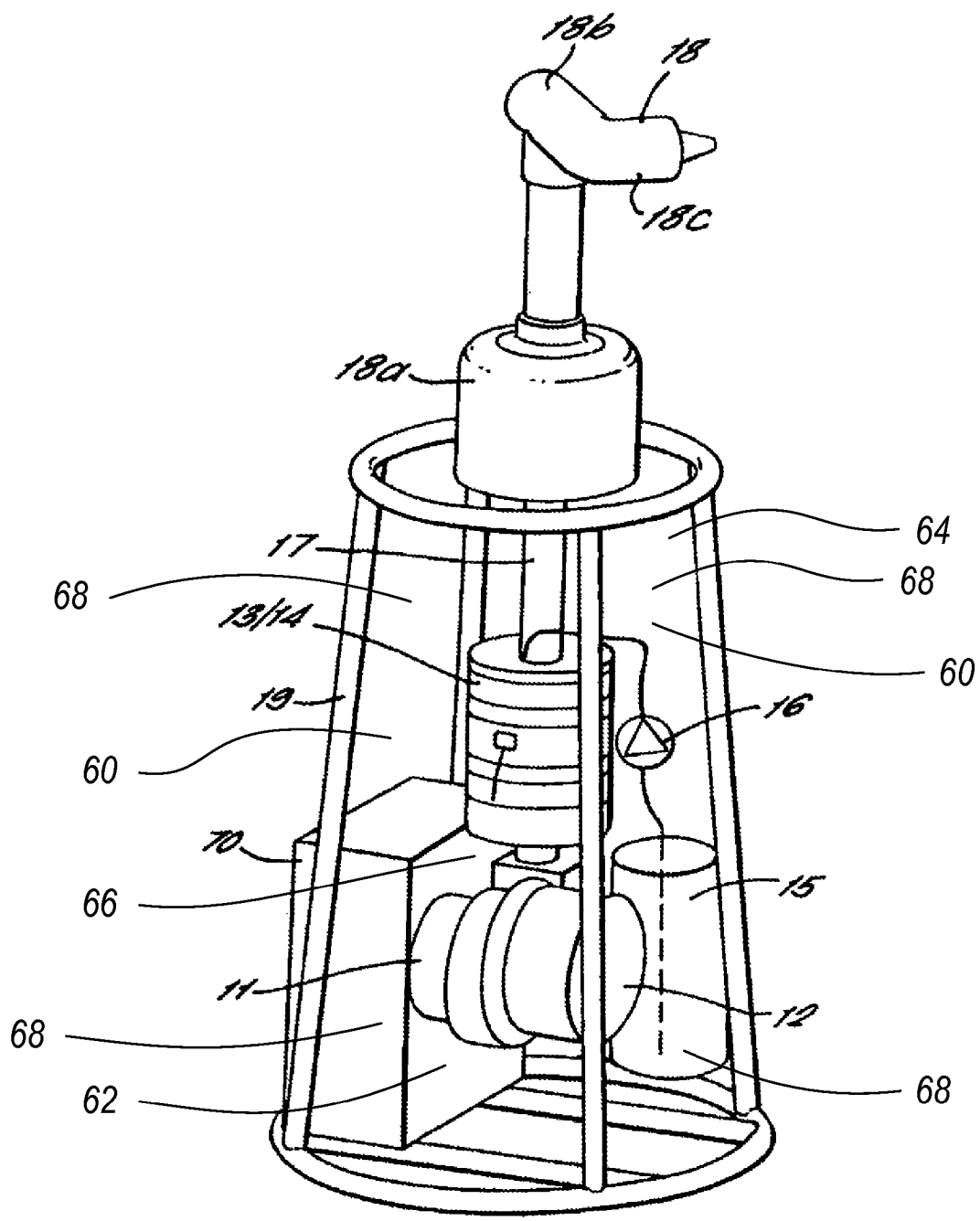
Figure 4:
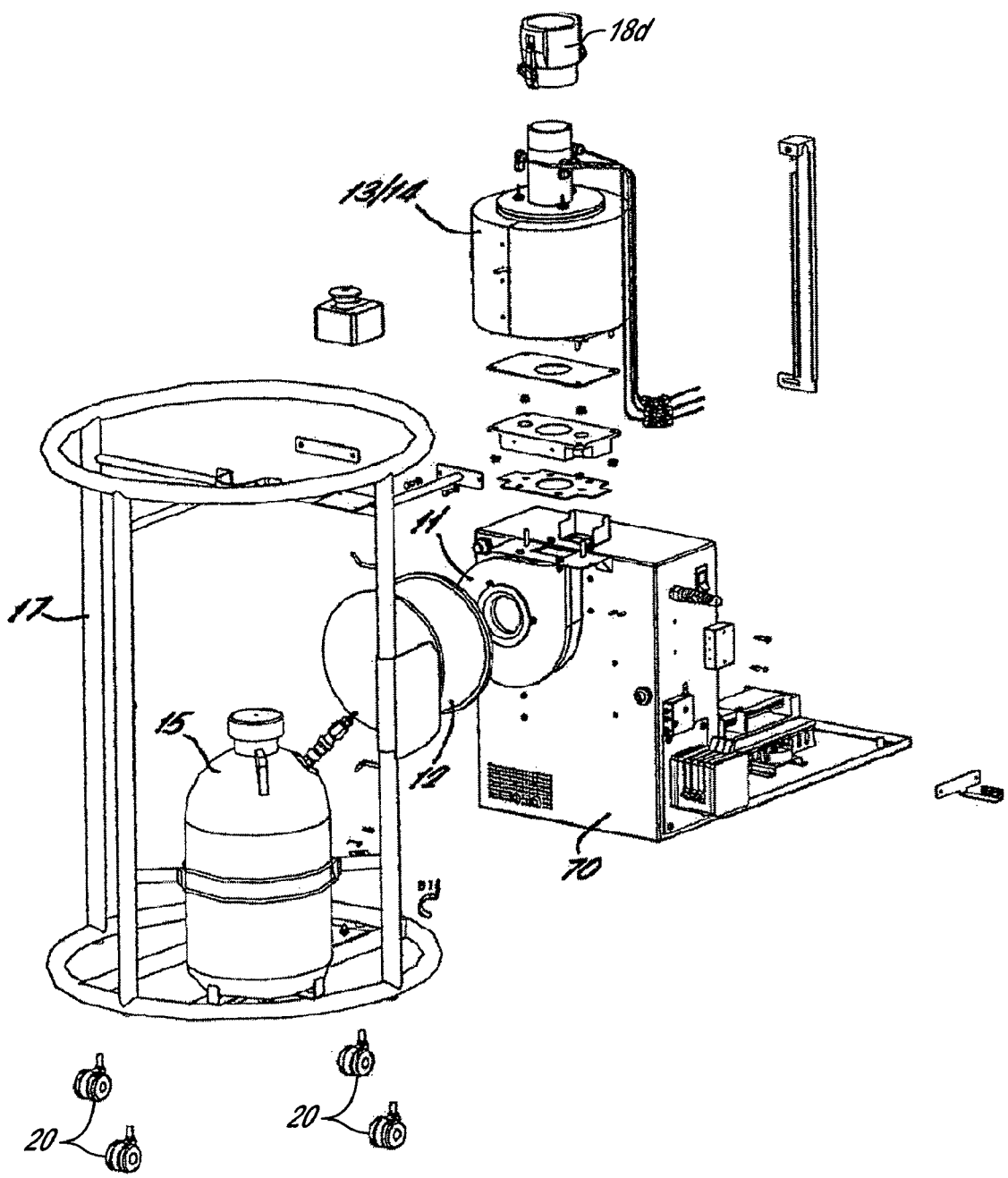

FIGS. 3 and 4 show a practical embodiment in which the gas generator apparatus is supported in a tubular steel framework or structure 19 for ease of movement. Structure 19 has opposing lateral sides 60 that each extend between a front side 62 and an opposing back side 64. The structure 19 at least partially bounds a compartment 66 and has a plurality of spaced apart openings 68 that communicates between the exterior atmosphere and compartment 66. As shown in the depicted embodiment, each side may incorporate a separate one of the openings 68. One or more of the gas generator apparatus components may be disposed within compartment 66. For example, as shown in the depicted embodiment, HEPA filter 11, fan 12, heater 13, flash evaporator 14, container 15, liquid pump 16, and/or conduit 17 may be wholly or partially disposed within compartment 66 so that respective exterior surfaces thereof are freely exposed to the exterior atmosphere by way of the plurality of openings 68. The apparatus is light enough to be carried by the user and as can be seen in FIG. 4 can have caster wheels 20 to enable it to be easily manoeuvred into position. The tubular framework is sealed to prevent any contamination being introduced to the enclosure by the frame. Ideally, the apparatus should not be placed inside a housing unit. Any covering of the apparatus would restrict the sterilant gas movements around and through the apparatus, which is essential to ensure that the apparatus itself is also surface decontaminated because otherwise it may contaminate the area in which it is placed. FIGS. 3 and 4 also show the enclosed control box 70 for the apparatus disposed at least partially within compartment 66 so that the exterior surface of control box 70 is also freely exposed to the exterior atmosphere by way of the plurality of openings 68. Control box 70 will be described in greater detail below.

FIG. 3 shows the outlet nozzle in greater detail. The nozzle has a motorised power unit 18a which rotates the nozzle assembly about a vertical axis. The nozzle assembly includes a laterally extending arm 18b having an enclosed drive for rotating the nozzle tip 18c about a horizontal axis to provide a universal discharge of heated air/hydrogen peroxide sterilant vapour around the room or other enclosure. The motor and nozzle assembly are formed as a unit and may be detached at the coupling 18d shown in FIG. 4 from the outlet of the evaporator and dismounted from the frame to be transported independently of the gas generator unit. Multiple units may be provided as necessary and separate fan units may also be provided to circulate the sterilant atmosphere throughout the room or enclosure.

An ideal decontamination cycle may have three distinct phases. In the first optional phase, the relative humidity in the room or other enclosure is adjusted to a pre-set level. In the second phase the gas concentration of sterilant gas is raised to form a required layer of condensation over all surfaces in the enclosure for a sufficient length of time to achieve the required level of decontamination. In the third and last phase the sterilant is removed from the enclosure. This is achieved using the room aerator system described and illustrated in International Patent Publication No. WO 02/11864.

If a HVAC system is available for the room or enclosure then this may be used to achieve the required level of relative humidity at the start of the process, and if the HVAC exhausts to a safe area to remove the sterilant at the end. Alternatively a portable dehumidifier may be used to adjust the initial relative humidity and a catalytic scrubber used to circulate the gas to remove the sterilant.

In the decontamination cycle referred to above the initial phase of treatment in the adjustment of the relative humidity in the room or chamber may be omitted and the process commenced at the current prevailing conditions in the enclosure since the relative humidity in the enclosure would normally be well below dew point and so a considerable amount of sterilant/water vapour would need to be generated in the enclosure before condensation would occur.

Figure 6:
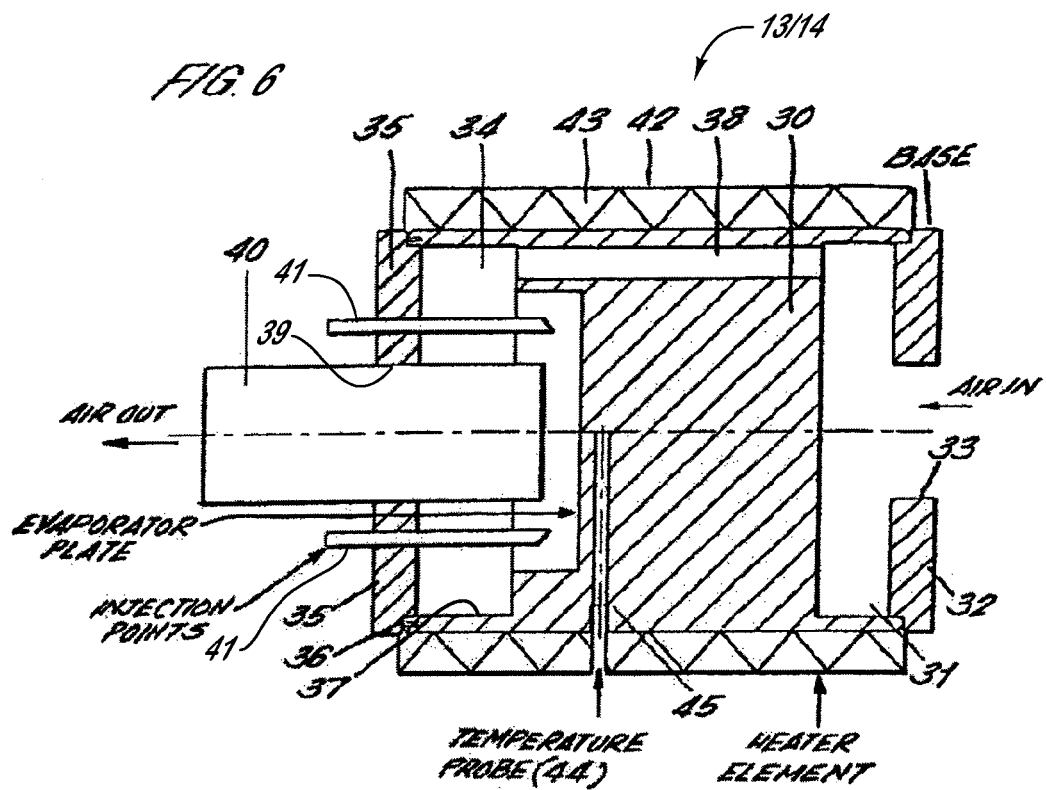
Figure 5:
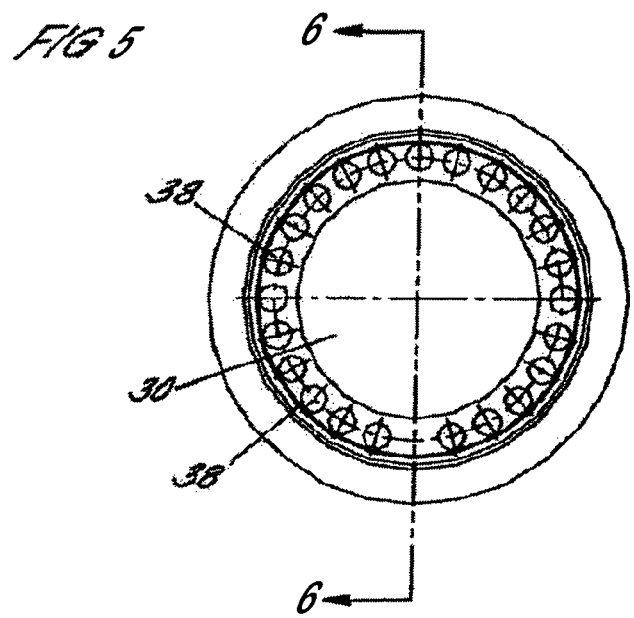

Reference is now made to FIGS. 5 and 6 which illustrate the combined heater/evaporator 13/14 in greater detail. The heater/evaporator comprises a cast cylindrical aluminium block 30 which is mounted in framework 19 with the axis of the block extending vertically. The lower end of the block has a shallow cylindrical recess 31 and a circular base plate 32 is attached to the periphery of the block extending across the recess by screws (not shown). The base plate 32 has a central aperture 33 in which the end of the inlet conduit 10 is mounted to deliver a supply of air to the recess in the block.

The upper end of the block also has a cylindrical recess 34 and a central top plate 35 is mounted on the periphery of the block over the recess by set screws 36. The top plate 35 has a central aperture 39 in which an outlet conduit 40 from the block is mounted.

The block is formed with a central cylindrical cavity 37 extending into the block from the upper end thereof in which the outlet conduit 40 extends stopping short of the bottom of the cavity. The block 30 has a multiplicity of axially extending passageways 38 adjacent the outer surface of the block and spaced around the block leading from the lower recess 31 and the block upper recess 34 for flow of air from the bottom recess to the top recess from where the air can flow into the cavity 37 and thence into the outlet conduit 40. The liquid sterilant from the storage container 15 is delivered via one or more inlet conduits 41 providing injection points which extend through the top plate 35 adjacent to the outlet conduit 40. The conduits 41 lead into the cavity 37 in the block but stop short of the bottom of the cavity. A second inlet conduit 41 is shown and preferably three such conduits are provided at spaced locations around the outlet conduit.

The body 30 is encircled by a cylindrical jacket in which an electrical resistance heater 42 is mounted for heating the body 30 to a requisite temperature to pre-heat the airflow through the block and also to ensure that sterilant delivered by the conduit 41 to the bottom of the cavity 37 of the block is flash evaporated from the bottom of the cavity to produce a vapour which is entrained in the flow of air through the flow of heated air through the outlet conduit 40 for delivery into the room to be sterilised.

The heating unit of the heater-evaporator is coupled to the control unit to the apparatus and a temperature probe 44 is mounted in a radial drilling 45 in the body 30 below the cavity 37 to measure the temperature of the body for adjusting, through the thereof in which the outlet conduit 40 extends stopping short of the bottom of the cavity. The block 30 has a multiplicity of axially extending passageways 38 adjacent the outer surface of the block and spaced around the block leading from the lower recess 31 and the block upper recess 34 for flow of air from the bottom recess to the top recess from where the air can flow into the cavity 37 and thence into the outlet conduit 40. The liquid sterilant from the storage container 15 is delivered via one or more inlet conduits 41 which extend through the top plate 35 adjacent to the outlet conduit 40 and also lead into the cavity 37 in the block and again stop short of the bottom of the cavity. A second such inlet conduit 41 is shown in dotted outline and preferably three such conduits are provided at spaced locations around the inlet conduit.

The body 30 is encircled by a cylindrical jacket in which an electrical resistance heater 42 is mounted for heating the body 30 to a requisite temperature to pre-heat the airflow through the block and also to ensure that sterilant delivered by the conduit 14 to the bottom of the cavity 37 of the block is flash evaporated from the bottom of the cavity to produce a vapour which is entrained in the flow of air through the flow of heated air through the outlet conduit 40 for delivery into the room to be sterilised.

The heating unit of the heater-evaporator is coupled to the control unit to the apparatus and a temperature probe 44 is mounted in a radial drilling 45 in the body 30 below the cavity 37 to measure the temperature of the body for adjusting, through the control unit, the power supply to the resistance heating element to enable the body to be maintained at a requisite temperature for pre-heating the air flowing through the body and flash evaporating the sterilant delivered to the body.

FIG. 7 of the drawings shows an alternative form of heater 13 in which the outlet from the fan 12 is coupled to an inlet 50 to a lower chamber 51 containing an electrically powered air heater 52. At the upper end of the chamber 51 there is an annular evaporator block 53 having a central port 54 for gas flow and an evaporator plate 55 is located on top of the block. The block has a spirally wound heating element 56 embedded adjacent the surface of the block. Thus the heater 52 can be used to raise the temperature of the air flowing through the device to one level and the second heater 56 can be used to maintain the surface of the evaporator plate at the requisite temperature for flash evaporation of an aqueous solution of hydrogen peroxide.

The heater has an upper chamber 57 in which an outlet conduit 58 is mounted having ports 59 spaced around the conduit through which air can enter the conduit from the upper chamber as indicated by the arrows. The lower end of the conduit is closed by an air deflector 61 which partially overlies the evaporation plate and causes the air flow emerging from the port 54 in the evaporator heater to disperse outwardly over the evaporator plate before flowing upwardly and hence through the port 59 into the inlet conduit. Delivery tubes for aqueous hydrogen peroxide extend downwardly through the upper chamber 57 to stop just short of the surface of the evaporation plate to drip aqueous hydrogen peroxide onto the plate which flash evaporates and is entrained in the air flow over the plate which passes upwardly into the outlet conduit 58. The arrangement is otherwise similar to that of FIGS. 3 and 4.

Figure 8:
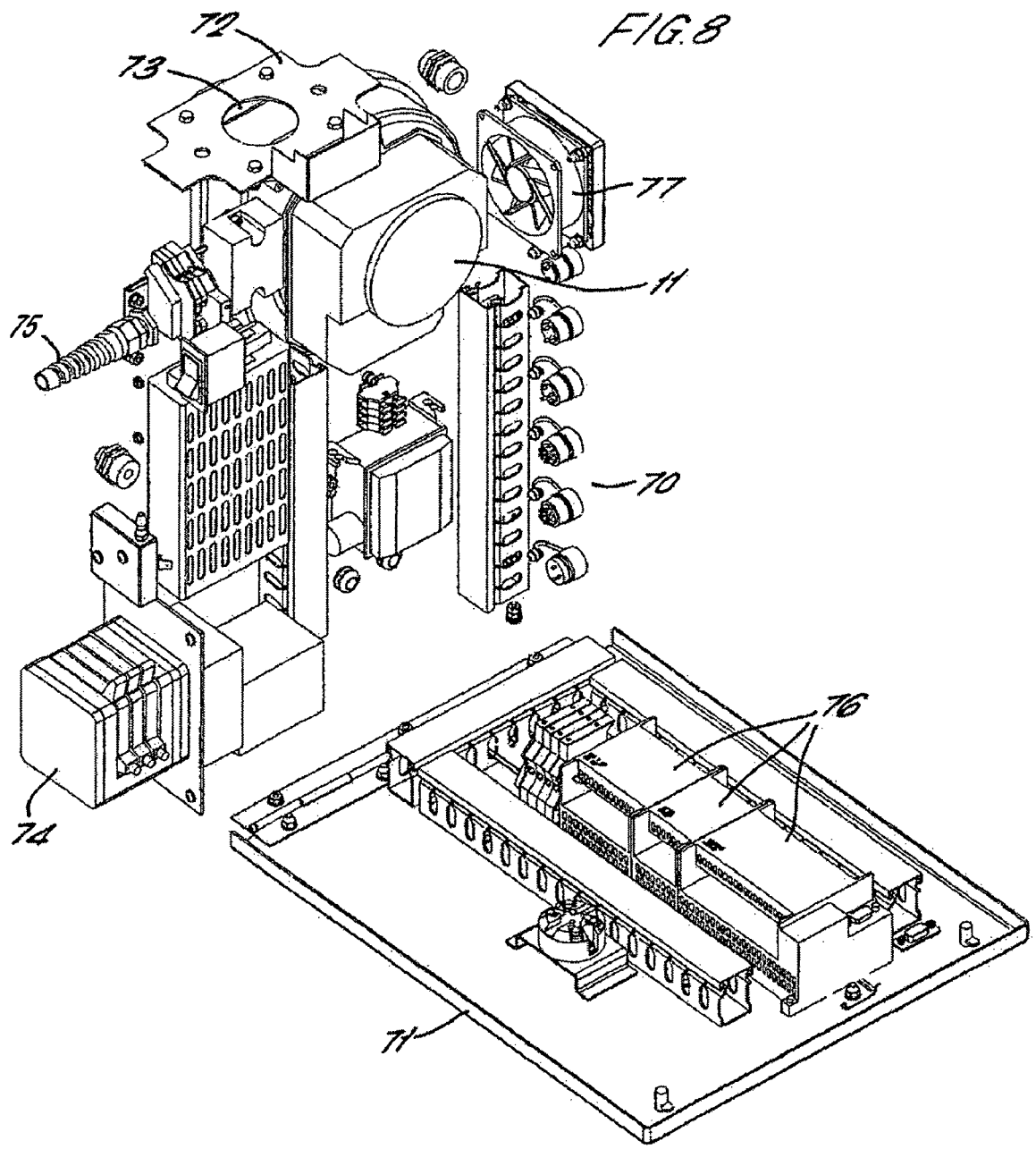

Reference is now made to FIG. 8 of the drawings which shows the control box of the gas generator of FIGS. 3 and 4 in greater detail. The control box comprises a casing 70 having a lid 71 shown in the open position in FIG. 8. The fan 11 which is of the centrifugal type is mounted in the upper end of the box and has an upwardly facing mounting plate 72 formed with an outlet port 73 to receive the evaporator 13, 14 with the inlet to the evaporator in communication with the port 73.

A liquid pump 74 is mounted on one side of the box powered by an electric motor for delivering aqueous hydrogen peroxide to the evaporator. A mains cable connection for the unit for the various motors and other devices requiring power supply is indicated at 75. The cable also provides couplings to the controllers 76 for the unit which are mounted on the inside of the lid 71.

To ensure that contamination does not reach the enclosure from the interior of the control box for the gas generator, a fan 77 is mounted on one side of the control box to deliver air carrying sterilant from the surrounding atmosphere in the enclosure through the control box to sterilise the interior surfaces of the control box.

Figure 9:
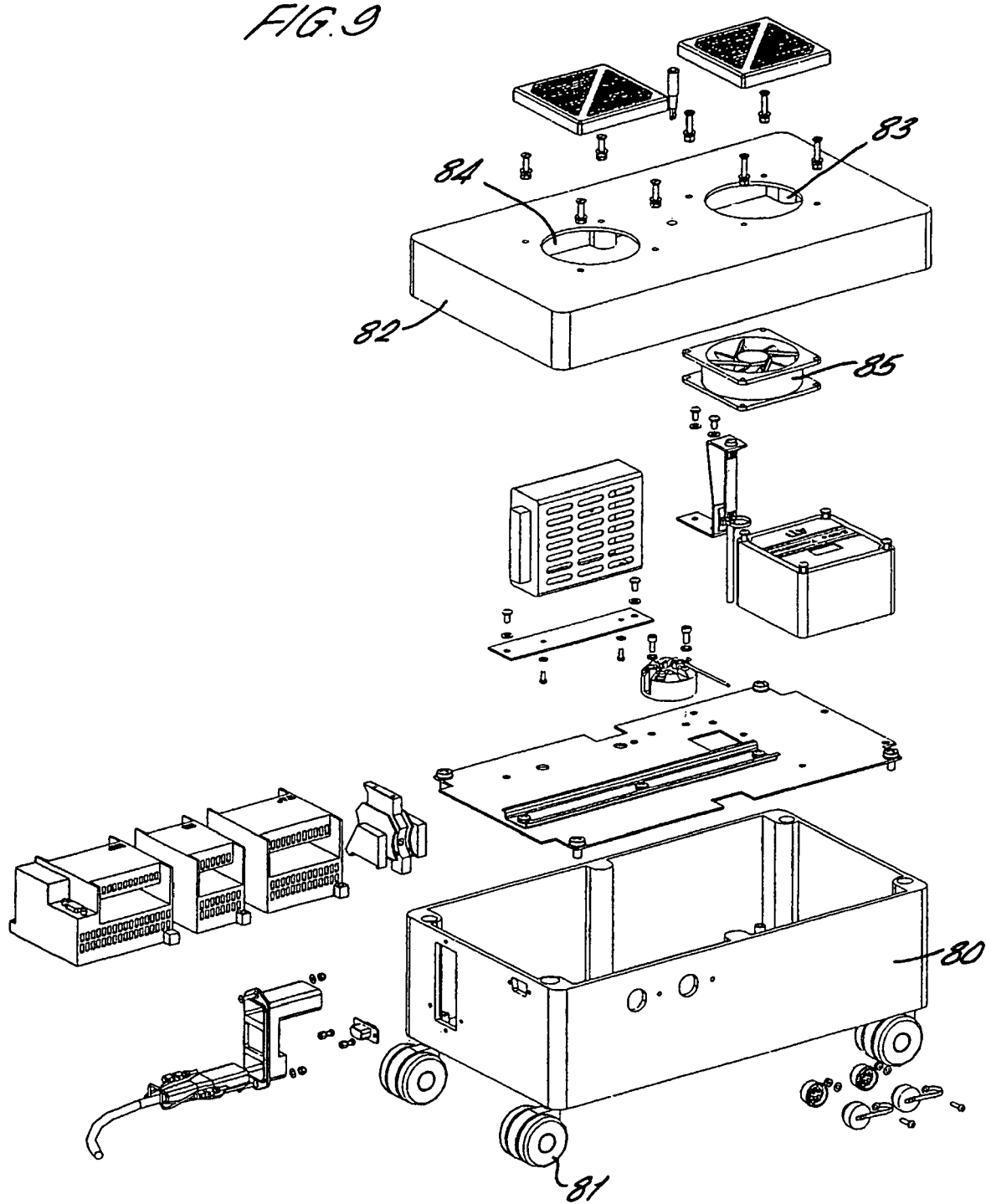

Reference is now made to FIG. 9 of the drawings which shows in exploded form a monitoring unit for monitoring air temperature, gas concentration and humidity in the enclosure. The monitoring unit comprises a box 80 to receive the monitoring equipment and mounted on wheels 81 to enable the box to be readily manoeuvred around the enclosure and also moved from side to side where it is to be used. The box has a lid 82 formed with inlet and outlet ports 83, 84 respectively. The inlet port has a motor driven fan 85 disposed below the port to draw in air from the enclosure containing the dispersed sterilant to cause an air flow through the elements in the box to sterilise the interior surfaces of the box and thereby to ensure that the room or other enclosure is not contaminated by anything within the interior of the box.

The apparatus described particularly with reference to FIGS. 3 to 9 is intended to be readily portable or transportable from room to room where it is to be used. It provides a source of heated air carrying hydrogen peroxide vapour sterilant directly into the room and distributes the air flow throughout the room until condensation occurs on all surfaces within the room. This includes the exposed exterior surfaces of the components disposed within compartment 66 of the apparatus by virtue of the hydrogen peroxide vapour sterilant passing through openings 68. No external pipework connections are required to pass through walls of the room just power supply and control cables for the apparatus. No special installation requirements arise as in conventional gas generator circuit systems as referred to earlier.

Thus each of the components of the equipment required to sterilise a room, that is the gas generating apparatus, the gas distribution system, the instrument-module, the dehumidifier and the aeration unit are all manufactured such that they can readily be carried by a single person.

Figure 10:
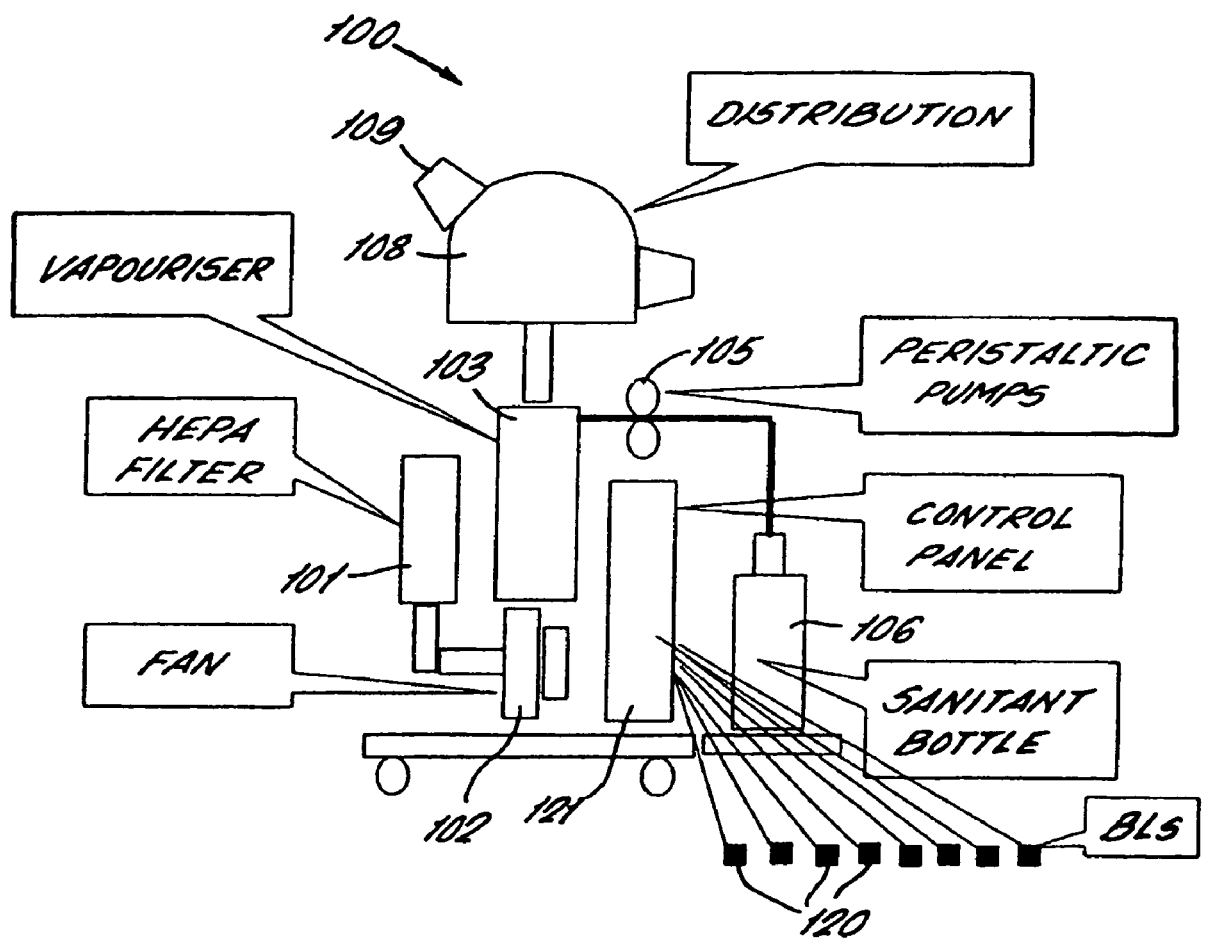

Reference is now made to a further form of apparatus in accordance with the invention shown in FIG. 10. The apparatus is mounted on a mobile trolley and comprises a gas generator 100. Air is drawn in through a HEPA filter 101 by a fan 102 and passed into a vaporiser 103. Inside the vaporiser the air is first heated by a heater (not shown) and then passes over an evaporation plate (also not shown) A pump 105 delivers liquid sanitant from a sanitant bottle 106 in the form of droplets onto the evaporation plate from which it is flash evaporated. The heated air carrying the sanitant vapour is passed to a distribution plenum 108 and exits to the room at high velocity through one or more nozzles 109.

Provision is made either to connect a number of optical type condensation monitors 120 directly to the gas generator and hence to a control module 121 (see FIG. 11), or the monitors may be connected directly to the control module. The optical condensation monitors measure the layer of condensation as it builds up on a surface or surfaces of the monitor. Connecting condensation monitors to the gas generator has the advantage of reducing the number of connections to the control module, especially when a number of gas generators are used.

The condensation monitors are placed around the room at the locations where the rate of condensation is the lowest.

Figure 11:
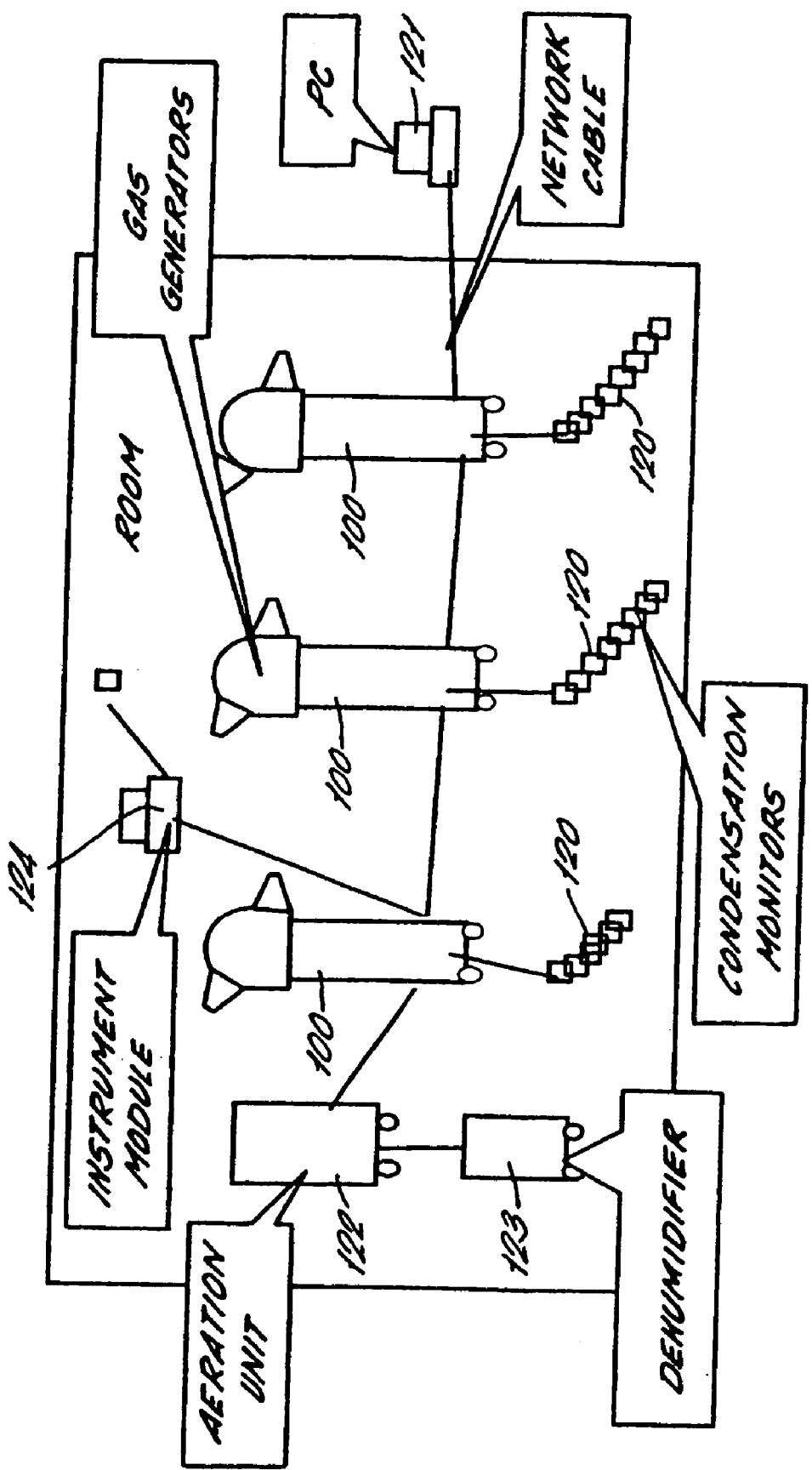

A complete multiple installation is shown in FIG. 11, with three gas generators 100 each with eight condensation monitors 120. Also connected to the control system is an aeration unit 122 used to remove the gas at the end of the cycle and the dehumidifier 123. A separate instrument module 124 is also shown which has additional instrumentation to measure the gas concentration and the RH within the room. A single communications cable connects 24 all of the components to the control module.

The normal technique to establish if a decontamination process has been successful is to place Biological Indicators (BIs), in those parts of the chamber where it is the most difficult to achieve a kill. It is often undesirable or not permitted to place BIs in a room, but it is necessary to know that deactivation to the required level has been achieved. To overcome this difficulty condensation monitors may be used to establish that the mass and the rate of formation of condensate are sufficient to achieve deactivation of the microorganisms on the surfaces. It has been well established that once the required conditions have been achieved that the "D" value for the most resistant organisms is about two minutes. Therefore an exposure of the organisms under the correct conditions for twelve minutes will achieve a log 6 reduction in the count of viable organisms.

Satisfactory decontamination will only be achieved in a room if a sufficiently high rate of liquid sanitant vapour is delivered into the room to provide an adequate rate of formation of condensation. But to be assured that decontamination has been achieved it is necessary to measure the condensation levels with time in multiple locations in the room. The data from the condensation monitors together with the information from the other instruments in the room may then be used to establish that a satisfactory deactivation cycle has been completed.

The condensation sensors may be used in one of two ways. The first is to measure and then control the level of condensation by adjusting the liquid evaporation rate and the second is simply to use the monitor as a switch. When used as a switch it simply gives a signal when an adequate amount of condensation has formed and the process is then considered to be complete or allowed to dwell in that state giving a sufficient period during which the organisms are killed. There is a further variation to the "switch" method in which two sensors are used at each location set at different levels of condensation. The first indicates when condensation has started and the second when the level of condensation is sufficient to have caused a satisfactory level. It may then be necessary to have a "dwell" period during which the kill occurs.

The condensation monitors of the above apparatus are optical devices which measure the layer of condensation. An electronic device may be used instead that gives a switch signal when a known level of condensation has arrived. The switch level depends on the construction of the sensor plate. Sensor plates are single use disposable items and hence are inexpensive. The plates plug into a box which may be placed at a remote location within the room.

The invention claimed is:

1. A method of decontaminating an enclosed space, the method comprising the steps of:
   positioning an apparatus within an enclosed space having an atmosphere, the apparatus including a structure at least partially bounding a compartment, the structure having a plurality of spaced apart openings that communicate between the compartment and the atmosphere within the enclosed space, a flash evaporator chamber being disposed within the compartment of the structure, the flash evaporator chamber having an exterior surface that is freely exposed to the atmosphere within the enclosed space by way of the plurality of spaced apart openings;
   creating a recirculating heated airstream within the enclosed space by the apparatus performing the following:
      (i) continuously drawing air from the atmosphere within the enclosed space to form an air stream,
      (ii) heating the airstream while in the enclosed space, and
      (iii) emitting the heated airstream back into the atmosphere within the enclosed space; and
   progressively introducing a hydrogen peroxide and water vapour mixture into the recirculating heated airstream until the atmosphere within the enclosed space reaches a dew point that causes the hydrogen peroxide and water vapour mixture within the atmosphere to simultaneously and continuously condense onto substantially all exposed surfaces bounding or within the enclosed space so as to decontaminate the surfaces, the hydrogen peroxide and water vapour mixture passing through the plurality of openings of the structure to condense on the exterior surface of the flash evaporation chamber, the hydrogen peroxide and water vapour mixture being produced by flash evaporating within the flash evaporation chamber an aqueous solution of hydrogen peroxide, the step of progressively introducing the hydrogen peroxide and water vapour mixture into the recirculating heated airstream being performed by the apparatus that is disposed within the enclosed space.

2. The method as claimed in claim 1, further comprising removing the hydrogen peroxide from the enclosed space after the dew point has been reached and the hydrogen peroxide and water mixture has condensed on the surfaces.

3. The method as claimed in claim 2, further comprising:
   measuring the condensation of the hydrogen peroxide and water vapour mixture on the surfaces by a monitor; and
   terminating the step of introducing the hydrogen peroxide and water vapour mixture into the recirculating heated airstream when the measured condensation has reached a predefined level.

4. The method as claimed in claim 2, further comprising measuring the condensation in the enclosed space at a number of different locations by condensation monitors to ensure that condensation has taken place throughout the enclosed space.

5. The method as claimed in claim 1, further comprising terminating the step of introducing the hydrogen peroxide and water vapour mixture into the recirculating heated airstream when a predetermined concentration of the hydrogen peroxide and water vapour mixture vapour in the atmosphere has been reached.

6. The method as claimed in claim 5, further comprising:
using biological indicators in the enclosed space to determine when the predetermined concentration of the hydrogen peroxide and water vapour mixture in the atmosphere has been reached; and
removing the hydrogen peroxide from the enclosed space after the hydrogen peroxide and water vapour mixture has reached the predetermined concentration.

7. The method as claimed in claim 1, further comprising delivering the heated airstream carrying the hydrogen peroxide and water vapour mixture as a jet within the enclosed space.

8. The method as claimed in claim 7, further comprising delivering the heated airstream carrying the hydrogen peroxide and water vapour mixture in a universally rotating jet to distribute the hydrogen peroxide and water vapour mixture throughout the enclosed space.

9. The method as claimed in claim 1, further comprising using one or more fans within the enclosed space to disperse the hydrogen peroxide and water vapour mixture throughout the enclosed space.

10. The method as claimed in claim 1, wherein the aqueous solution of hydrogen peroxide from which the hydrogen peroxide and water vapour mixture is produced contains 30 to 35% hydrogen peroxide and a balance of water.

11. The method as claimed in claim 1, wherein the hydrogen peroxide and water vapour mixture further comprises peracetic acid.

12. The method as claimed in claim 11, wherein the aqueous solution of hydrogen peroxide from which the hydrogen peroxide and water vapour mixture is produced comprises 15% hydrogen peroxide, 0.5% peracetic acid and a balance of water.

13. The method as claimed in claim 1, further comprising removing the hydrogen peroxide by circulating the atmosphere containing the hydrogen peroxide and water vapour mixture over a catalyst.

14. The method as claimed in claim 1, further comprising removing the hydrogen peroxide from the enclosed space by using a heating/ventilation air conditioning system communicating with the enclosed space.

15. The method as claimed in claim 1, further comprising:
forming a plurality of separate recirculating heated airstreams within the enclosed space; and
progressively introducing the hydrogen peroxide and water vapour mixture into each of the plurality of separate recirculating heated airstreams, the steps of forming a plurality of separate recirculating heated airstreams and progressively introducing the hydrogen peroxide and water vapour mixture into each of plurality of separate heated airstreams being performed by apparatuses that are disposed within the enclosed space.

16. The method as claimed in claim 1, further comprising controlling the steps of creating a recirculating heated airstream and progressively introducing the hydrogen peroxide and water vapour mixture from outside the enclosed space.

17. The method as claimed in claim 1, further comprising dehumidifying the atmosphere within the enclosed space to reduce the relative humidity thereof to a predetermined level prior to progressively introducing the hydrogen peroxide and water vapour mixture into the recirculating heated airstream.

18. The method as claimed in claim 17, further comprising using an air conditioning system to dehumidify the atmosphere within the enclosed space.

19. The method as claimed in claim 1, wherein the steps of creating a recirculating heated airstream and progressively introducing the hydrogen peroxide and water vapour mixture into the recirculating heated airstream are performed by a portable apparatus in the enclosed space having a duct with a fan for delivering air through the duct, a filter for filtering air entering the duct, a heater for heating air passing through the duct and means for delivering the hydrogen peroxide and water vapour mixture to the air passing through the duct and a nozzle for delivery of air carrying the hydrogen peroxide and water vapour mixture from the duct, the nozzle being rotated universally to distribute the hydrogen peroxide and water vapour mixture throughout the enclosed space, circulation of air carrying the hydrogen peroxide and water vapour mixture through the duct causing decontamination of the duct.

20. The method as claimed in claim 1, wherein the hydrogen peroxide and water vapour mixture uniformly condenses on all of the surfaces within the enclosed space.

21. The method as claimed in claim 1, wherein the structure includes a front side and an opposing back side, each having at least one of the openings formed therethrough, the hydrogen peroxide and water vapour mixture passing through the openings of the front and back sides of the structure to condense on the exterior surface of the flash evaporation chamber.

22. The method as claimed in claim 21, wherein the structure also includes opposing lateral sides extending between the front and back sides, the lateral sides each having at least one of the openings formed therethrough, the hydrogen peroxide and water vapour mixture also passing through the openings of the lateral sides of the structure to condense on the exterior surface of the flash evaporation chamber.

23. The method as claimed in claim 1,
wherein a conduit, a fan, and a container holding hydrogen peroxide are disposed within the compartment of the structure and each has an exterior surface that is freely exposed to the atmosphere within the enclosed space by way of the plurality of spaced apart openings, and
wherein progressively introducing the hydrogen peroxide and water vapour mixture into the recirculating heated airstream causes the hydrogen peroxide and water vapour mixture to pass through the plurality of openings of the structure to condense on the exterior surfaces of the conduit, the fan, and the container.

24. The method as claimed in claim 1,
wherein a control box for controlling operation of the apparatus is disposed within the compartment of the structure, the control box having an exterior surface that is freely exposed to the atmosphere within the enclosed space by way of the plurality of spaced apart openings, and
wherein progressively introducing the hydrogen peroxide and water vapour mixture into the recirculating heated airstream causes the hydrogen peroxide and water vapour mixture to pass through the plurality of openings of the structure to condense on the exterior surface of the control box.

25. The method as claimed in claim 24,
wherein the control box bounds an enclosed interior space and includes means for delivering the heated airstream through the interior space, and
wherein progressively introducing the hydrogen peroxide and water vapour mixture into the recirculating heated airstream causes the hydrogen peroxide and water vapour mixture to pass through the control box by way of the means for delivering the heated airstream to condense on interior surfaces of the control box.

26. A method of decontaminating an enclosed space, the method comprising the steps of:
  positioning a portable decontamination apparatus within an enclosed space having an atmosphere, the decontamination apparatus including a structure at least partially bounding a compartment, the structure having a plurality of spaced apart openings that communicate between the compartment and the atmosphere within the enclosed space, a flash evaporator chamber being disposed within the compartment of the structure, the flash evaporator chamber having an exterior surface that is freely exposed to the atmosphere within the enclosed space by way of the plurality of spaced apart openings;
  activating the decontamination apparatus so that the decontamination apparatus performs the following functions within the enclosed space:
    (i) continuously drawing air from the atmosphere within the enclosed space to form an air stream within the decontamination apparatus;
    (ii) heating the airstream within the decontamination apparatus;
    (iii) flash evaporating within the flash evaporator chamber an aqueous solution of hydrogen peroxide to form a hydrogen peroxide and water vapour mixture;
    (iv) introducing the hydrogen peroxide and water vapour mixture into the heated air stream; and
    (v) emitting the heated air stream containing the hydrogen peroxide and water vapour mixture from the decontamination apparatus and into the atmosphere of the enclosed space; and
  operating the decontamination apparatus positioned within the enclosed space until the atmosphere within the enclosed space reaches a dew point that causes the hydrogen peroxide and water vapour mixture within the atmosphere to simultaneously and continuously condense onto substantially all exposed surfaces bounding or within the enclosed space so as to decontaminate the surfaces, the hydrogen peroxide and water vapour mixture passing through the plurality of openings of the structure to condense on the exterior surface of the flash evaporation chamber.

27. The method as recited in claim 26, further comprising passing the air through a filter as the air is drawn from the atmosphere into the decontamination apparatus.

28. The method as recited in claim 26, wherein the step of emitting the heated air stream comprises passing the heated air stream out of the decontamination apparatus through a rotating nozzle.

29. The method as claimed in claim 26, wherein the hydrogen peroxide and water vapour mixture further comprises peracetic acid.

30. The method as claimed in claim 26, further comprising activating a plurality of the portable decontamination apparatus positioned within the enclosed space.

31. The method as claimed in claim 26, further comprising:
  measuring the condensation of the hydrogen peroxide and water vapour mixture on the surfaces; and
  terminating the step of introducing the hydrogen peroxide and water vapour mixture into the heated airstream when the measured condensation has reached a predefined level.

32. The method as claimed in claim 26, further comprising removing the hydrogen peroxide from the enclosed space after the surfaces have been decontaminated.

33. The method as claimed in claim 32, further comprising removing the portable decontamination apparatus from the enclosed space after the hydrogen peroxide is removed from the enclosed space.

34. The method as claimed in claim 26, further comprising positioning the portable decontamination apparatus within a room, the walls of the room bounding the enclosed space.

35. The method as claimed in claim 26, wherein the hydrogen peroxide and water vapour mixture uniformly condenses on all of the surfaces within the enclosed space.

36. The method as recited in claim 26,
  wherein the structure includes a front side and an opposing back side, each having an opening formed therethrough, and
  wherein operating the decontamination apparatus causes the hydrogen peroxide and water vapour mixture to pass through the openings of the front and back sides of the structure and condense on the exterior surface of the flash evaporation chamber.

37. The method as recited in claim 36,
  wherein the structure also includes opposing lateral sides extending between the front and back sides, the lateral sides each having an opening formed therethrough, and
  wherein operating the decontamination apparatus also causes the hydrogen peroxide and water vapour mixture to pass through the openings of the lateral sides of the structure and condense on the exterior surface of the flash evaporation chamber.

38. The method as claimed in claim 26,
  wherein a conduit, a fan, and a container holding hydrogen peroxide are disposed within the compartment of the structure and each has an exterior surface that is freely exposed to the atmosphere within the enclosed space by way of the plurality of spaced apart openings, and
  wherein operating the decontamination apparatus causes the hydrogen peroxide and water vapour mixture to pass through the plurality of openings of the structure to condense on the exterior surfaces of the conduit, the fan, and the container.

39. The method as claimed in claim 26,
  wherein a control box for controlling operation of the apparatus is disposed within the compartment of the structure, the control box having an exterior surface that is freely exposed to the atmosphere within the enclosed space within the enclosed space by way of the plurality of spaced apart openings, and
  wherein operating the decontamination apparatus causes the hydrogen peroxide and water vapour mixture to pass through the plurality of openings of the structure to condense on the exterior surface of the control box.

40. The method as claimed in claim 39,
  wherein the control box bounds an enclosed interior space and includes means for delivering the heated airstream through the interior space, and
  wherein operating the decontamination apparatus causes the hydrogen peroxide and water vapour mixture to pass through the control box by way of the means for delivering the heated airstream and condense on interior surfaces of the control box.

* * * * *

UNITED STATES PATENT AND TRADEMARK OFFICE
CERTIFICATE OF CORRECTION

PATENT NO. : 7,790,104 B2
APPLICATION NO. : 10/509192
DATED : September 7, 2010
INVENTOR(S) : Adams et al.

Page 1 of 1

It is certified that error appears in the above-identified patent and that said Letters Patent is hereby corrected as shown below:

On the Title page:
Item 56, References Cited, OTHER PUBLICATIONS, Page 2
Right Hand Column, change the reference "Seymour S. Block, Ph.D., *Disinfection, Sterilization, and Preservation*, $5^{th}$ Edition, Lippincott Williams & Wilkins, Dec. 200, pp. 188-189." to --Seymour S. Block, Ph.D., *Disinfection, Sterilization, and Preservation*, $5^{th}$ Edition, Lippincott Williams & Wilkins, Dec. 2000, pp. 188-189.--

Column 2
Line 61, change "described patent" to --described in patent--

Column 4
Line 51, change "in" to --is--

Column 7
Line 10, change "through the thereof" to --through thereof--
Line 28, change "conduit 14" to --conduit 40--

Column 8
Line 64, change "shown) A" to --shown). A--

Column 9
Line 22, after "connects" remove --24--

Column 14
Lines 47-48, change "within the enclosed space within the enclosed space" to --within the enclosed space--

Signed and Sealed this
Twenty-fourth Day of May, 2011

David J. Kappos
*Director of the United States Patent and Trademark Office*